United States Patent [19]

Bieber et al.

[11] 4,381,292

[45] Apr. 26, 1983

[54] ANTI-HUMAN T-LYMPHOCYTE MONOCLONAL ANTIBODY

[75] Inventors: Charles P. Bieber, Los Altos Hills; Frank D. Howard, Los Altos, both of Calif.

[73] Assignee: The Board of Trustees of the Leland Stanford Jr. University, Stanford, Calif.

[21] Appl. No.: 206,915

[22] Filed: Nov. 14, 1980

[51] Int. Cl.³ .................... A61K 43/00; A61K 39/00; G01N 33/54
[52] U.S. Cl. ........................................ 424/1; 424/1.5; 424/85; 435/2; 435/7; 435/172; 260/112 R
[58] Field of Search ............ G01N/33/48; 424/1, 1.5, 424/85-89, 93; 435/7, 948; 260/112 R

[56] References Cited

U.S. PATENT DOCUMENTS 4,196,265 1/1980 Koprowski .............................. 435/2

FOREIGN PATENT DOCUMENTS 18794 11/1980 European Pat. Off. ............ 435/240

OTHER PUBLICATIONS

Eur. J. Immunology 1979, 9:205–210, A. J. McMichael et al., "A Human Thymocyte Antigen Defined by a Hybrid Myeloma Monoclonal Antidoly".

Primary Examiner—Benjamin R. Padgett
Assistant Examiner—M. Moskowitz
Attorney, Agent, or Firm—Bertram I. Rowland

[57] ABSTRACT

Mammalian monoclonal antibodies specific for an antigen diagnostic for thymocytes, normal peripheral T cells and some null cells. The antibodies which distinguish among subpopulations of T cells, find use in assays, cell sorting, and immunosupression.

9 Claims, No Drawings

ANTI-HUMAN T-LYMPHOCYTE MONOCLONAL ANTIBODY

BACKGROUND OF THE INVENTION

1. Field of the Invention

The ability to specifically bind to antigens found in blood cell membranes offers numerous opportunities for diagnosis and treatment. It is found that as cells differentiate and mature, the surface antigens change so that by having a plurality of antibodies specific for a particular site, one can diagnose the number and character of the different blood cells present in a serum sample.

The discovery by Milstein and Kohler of hybridomas capable of producing monoclonal antibodies offers opportunities to produce antibodies specific for a single determinant site. While hybridomas provide for the generation of antibodies specific for a determinant site, the problem still remains of obtaining antibodies which allow for the desired differentiation. Since cells have a large number of surface antigens, and each of these antigens may have one or more determinant sites, one is dealing with a large population of antigenic sites. As the cells differentiate and mature, the surface antigens change. Therefore, in developing the monoclonal antibody, one must find the antibody which specifically binds to the antigen which is diagnostic of the particular cells or subpopulation of cells of interest.

2. Brief Description of the Prior Art

Evans et al. has developed T cell specific monoclonal antibodies which react with a series of cell surface molecules designated Leu-1, Leu-2, Leu-3 and Leu-4. Leu-1 and Leu-4 are present on all peripheral T cells, whereas Leu-2 and Leu-3 define functionally distinct T cell subpopulations. Human T cell differentiation antigens have been described using the T series monoclonal antibodies produced by Schlossman, Reinherz and their collaborators. Reinherz and Schlossman (1980) Cell 19:821. A E-rosette inhibition assay has been described by Bieber and Stinson (1979) J. Imm. Methods 30:329.

SUMMARY OF THE INVENTION

Mammalian monoclonal antibodies specific for an antigen site designated Leu-5 provide means for inhibiting rosette formation, distinguishing thymocytes from peripheral T cells and in the peripheral population distinguishing cytotoxic/suppressor cells from helper/inducer cells, in conjunction with other antisera. The subject compositions find use as immunosuppressants, and may be labeled for use in sorters, counters, or diagnostic assays determining blood cell populations.

DESCRIPTION OF THE SPECIFIC EMBODIMENTS

In accordance with the subject invention, mammalian monoclonal antibodies are provided which bind to a specific antigenic site of a surface antigen of lymphocytes, particularly the subpopulations of thymocytes and peripheral blood T cells. Binding of the monoclonal antibodies to the cells inhibits rosette formation, indicating that the surface antigen is either the receptor involved in rosette formation or is associated with rosette formation. The antigen is referred to as Leu-5.

The subject compositions are prepared by the fusion of mammalian lymphocytes sensitized to thymocytes with an appropriate myeloma cell line, culturing the fusion product in HAT medium and isolating colonies whose supernatants inhibit rosettes. The monoclonal antibodies can then be prepared by injection of the hybridoma cell into mice primed with Pristane and isolating the ascites fluid from the abdominal cavity.

The lymphocytes which are employed may be derived from any mammal, such as primates, humans, rodents, e.g. mice, rats and rabbits, bovine, canine, ovine, or the like. As appropriate, the host may be sensitized by injection of the immunogen, in this instance thymocytes, followed by a booster injection, and then isolation of the spleen. Alternatively, where it is desired to use the monoclonal antibodies in a mammalian host, it will be desirable, although not necessary, to sensitize spleen cells in vitro with the Leu-5 antigen, which has been modified by conjugation to antigenic or haptenic markers, so as to induce an immune response. The fusion may then be carried out in accordance with conventional techniques.

The mammalian monoclonal antibodies may be labeled with a wide variety of labels which find conventional use in counting, sorting, and in diagnostic assays. Various labels include fluorescent compounds, radioactive labels, enzymes, ferromagnetic labels, particles e.g. charcoal, dextran, or the like. In each case, the binding of the mammalian monoclonal antibody to the Leu-5 determinant site will provide for detection and assaying for cells having the Leu-5 determinant site. Furthermore, to the extent different types of cells have different levels of the Leu-5 determinant site, the mammalian monoclonal antibodies allow for distinguishing various subpopulations of thymocytes and T-cells.

A wide variety of immunoassay methods have been developed employing different labels bound to ligands and/or antibodies. With the subject antibodies, the label would be conjugated to the antibody in conventional ways. See, for example, U.S. Pat. No. Re. 29,169; 3,817,837; 3,949,064; 3,984,533; 3,996,345; 4,020,151; 4,061,466; 4,120,945 and 4,134,792, involving labeling of antibodies or use of antibodies in competitive assays.

The protocols will vary in accordance with the nature of the label and whether the method is homogeneous or heterogeneous. For the most part, the assays are carried out in an aqueous buffered medium at a pH in the range of about 5 to 10. In non-competitive assays, labeled antibody will be combined with the lymphocyte containing sample. After centrifugation to separate the cells, the antibody in the supernatant can be measured by means of the label. In competitive assays, binding of antibody to labeled ligand results in a change in signal. In this situation, the antibody may or may not be labeled. See particularly, U.S. Pat. Nos. 3,817,837 and 3,996,345. The mammalian monoclonal antibodies in accordance with this invention are characterized by being capable of inhibiting rosette formation. In addition, they specifically bind to both thymocytes and peripheral blood T cells. Of the peripheral blood lymphocytes, the mammalian monoclonal antibodies bind to substantially all of the lymphocytes which form rosettes.

The mammalian monoclonal antibodies to Leu-5 (anti(Leu-5)) do not bind to esterase positive, glass adherent human monocytes, nor to human or rhesus erythrocytes or platelets. No simultaneous staining of Ig+ or cells positive for the subject mammalian monoclonal antibodies was noted in unseparated peripheral blood lymphocytes stained sequentially for Ig and the subject antibodies. A distinct pattern of staining was apparent on lymphocytes capable of binding the subject mammalian monoclonal antibodies. The antigen Leu-5 was evenly distributed over the cell surface in a speckled pattern with the specks varying in size from barely visible to almost plaque like.

The subject mammalian monoclonal antibodies when administered to Rhesus monkeys were found to result in a pronounced lymphopenia within one hour of treatment. Rosette forming cells fell to substantially non-detectible levels within about 30 mins. The subject monoclonal antibodies were capable of lysing human thymocytes in the presence of rabbit complement, however, only at high concentrations.

The monoclonal antibodies when used as an immunosuppressant will normally be administered in a physiologically acceptable medium, e.g. phosphate buffered saline. The dose will conveniently be administered intravenously and generally at a rate of about 0.1 to 5 mg protein/kg host, usually 0.5 to 2.5 mg protein/kg host. The lymphopenia should be monitored and the antibodies administered as required.

The following examples are offered by way of illustration and not by way of limitation.

EXPERIMENTAL

The method of Oi and Herzenberg was used for the production of monoclonal antibody producing cell lines. (Oi and Herzenberg: 1980 In Selected Methods in Cellular Immunology, B. Mishell and S. Shiigi eds, W. H. Freeman, San Francisco, Calif.) AKR/j and Balb/c mice (Jackson Laboratories, Bar Harbor, Maine), were immunized by intraperitoneal injection of $1.2 \times 10$ fresh human thymocytes mixed with heat killed Bordetella pertussis bacteria. Three to eleven weeks later mice were boosted with $1 \times 10^7$ fresh thymocytes given intravenously. Spleen cells from immune mice were harvested three days after boosting. Cells from each strain were pooled and fused with NS-1 myeloma cell line at a ratio of $3 \times 10^8$ spleen cells to $1 \times 10^8$ myeloma parent cells. Polyethylene glycol 1500 was used as a fusing agent. Selection of NS-1: spleen cell hybrids for continued propagation was accomplished by culturing the fusion products in hypoxanthine-aminopterin-thymidine medium (HAT) until live growing colonies could be detected among the cell debris by phase contrast microscopy. After further culturing of the colonies in hypoxanthine-thymidine media to dilute out remaining intracellular aminopterin, the supernatants from the colony containing wells were assayed for rosette inhibition titer.

The assays are performed in histocompatability trays under oil using reconstituted frozen thymocytes as the rosetting cell. Each oil filled well was inoculated with 5 $\mu$l of hybridoma supernatant containing putative antibody, 1 $\mu$l of thymocytes suspended at $5 \times 10^6$ cells/ml in media 199 containing 10% fetal calf serum and incubated 16 hours at 4° C. Following incubation, one microliter of a 3% SRBC suspension in Hanks Balanced Salt Solution (HBSS) was added to each plate well and the plates immediately centrifuged at $200 \times g$ for 5 min. At the completion of the centrifugation, 1 $\mu$l of 0.5 glutaraldehyde was inoculated into each well in order to fix rosettes to the well bottom. The plates were inverted, transferred to a microscope stage and the concentration of antibody causing 100% rosette inhibition recorded.

Those colonies whose supernatants inhibited rosettes were cloned by limiting dilution on a feeder layer of thymocytes from four week old Balb/c mice. Clones producing supernatants which inhibited rosettes at a 1:20 dilution were selected for expansion and antibody production. Seven stable anti(Leu-5) producing clones were derived from AKR/j:NS 1 hybridomas and one from Balb/c:NS 1 hybridomas. One AKR/j:NS 1 and one Balb/c:NS 1 produced antibodies which precipitated goat antimouse $IgG_3$. The anti(Leu-5) antibodies were shown to be monoclonal as defined by two-dimensional polyacrylamide gel electrophoresis employing the method of Jones, ibid.

Once stable cell lines were established and characterized, anti(Leu-5) was produced in quantity by inoculating $1 \times 10^7$ anti(Leu-5) producing cultured hybridoma cells i.p. into mice primed 10 days prior to cell injection by i.p. injection of 0.5 ml of Pristane (2,6,10,14-tetramethylpentadecane). Abdominal swelling from ascites was generally apparent within 20 days of cell inoculation. At this time the abdominal cavity was tapped with a 21 gauge needle on a 10 ml syringe, the fluid removed, pooled and centrifuged at $100 \times g$. The pellet, containing myeloma cells, was resuspended and used to inject new Pristane primed mice. NS 1:Balb/c hybrid was injected into Balb/c mice and NS 1:AKR/j hybrid injected into AKR/j/Balb/c F1 hybrids. AntiLeu-5 was removed from ascitic fluids by binding to protein A derivatized sepharose 4B beads. Elution of antibody from the beads was accomplished by use of a 0.01 M acetate buffer pH 4.0. For ease of performance the protein A beads were generally placed in small ($1 \times 10$ cm) glass columns and the effluents monitored for optical density at 280 nm. Antibody content of protein A purified Ig was determined by UV spectrophotometric methods assuming an extinction coefficient of 14.

The properties of the two hybridoma antibodies are found in the following table.

TABLE 1

Properties of AntiLeu-5 Hybridoma Antibodies Used for Primate Studies

| Name | Isotype[1] | Antibodies RIT[2] Human | Rhesus | Microcytotoxicity[3] |
|------|----------|-------------------------|--------|----------------------|
| ATM 3.1 | 3 | .25 ug | 8.0 ug | 1.0 mg |
| ATM 3.2 | 3 | .10 ug | 2.8 ug | 0.5 mg |

| Name | Protein A Binding | Monoclonal Cell Lines Mouse Strain | Myeloma Line |
|------|-------------------|------------------------------------|--------------|
| ATM 3.1 | + | Balb/c | NS 1 |
| ATM 3.2 | + | AKR/j | NS 1 |

[1]Reactivity by double immunodiffusion analysis to anti-mouse gamma 1,2a,2b and 3.
[2]Concentration of ATM required to cause 100% rosette inhibition of either human or rhesus thymocytes.
[3]Microcytotoxicity - concentration of ATM needed to lyse human thymocytes in the presence of rabbit complement.

Specificity of anti(Leu-5) for peripheral blood lymphocyte populations (PBL) and for thymocytes was defined using fluorescence labeling techniques. Human and rhesus primate thymocytes were teased from finely minced portions of freshly excised thymus into phosphate buffered saline pH 7.4, filtered through mesh silk and adjusted to a concentration of $5 \times 10^6$ cell/ml. Human and rhesus primate PBL were isolated from heparinized venous blood drawn from healthy donors by density gradient centrifugation on Ficoll-Hypaque gradients and washed three times with PBS (Boyum (1968) J. Clin. Lab. Invest. 21 (Suppl) 97:1). PBL were separated into three aliquots. One, which underwent no further separation, was adjusted to $5 \times 10^6$ cells/ml in PBS and designated as unseparated PBL. The second was used to prepare glass adherent cells which were designated as monocytes. These cells were prepared by reconstituting PBL to $1\times10^7$/ml in RPMI 1640 containing 10% human AB serum. Aliquots of this latter sample were placed on glass slides in a closed moisture chamber and incubated 30 minutes at 37° C. Unbound cells were removed by washing the slides three times with cold PBS. A third PBL aliquot was used for preparation of E-rosette cell (E-RFC) enriched or depleted subpopulations according to the method of Dean et al., (1975) J. Immunol. 115:1449.

Enriched or depleted populations were resuspended at $5\times10^6$ cells/ml in PBS. Monocyte, unseparated, E-RFC enriched and E-RFC depleted PBL subpopulations and thymocytes were processed such that the percentage of cells, which reacted with anti(Leu-5), formed E rosettes or had surface immunoglobulin or esterase activity, could be enumerated.

Surface immunoglobulins were detected by a direct fluorescein labeling procedure in which 0.2 ml of cell suspension, washed once in PBS containing 0.01% sodium azide (PBS/azide) was pelleted by configuration. To the pellet was added 0.05 ml of rhodamine conjugated goat antihuman IgG (Cappel Laboratories, Cochranville, Pa.) diluted 1/10 in PBS/azide. The mixture was incubated 20 minutes at 4° C., then washed twice with cold PBS/azide. The pellet from the final wash was resuspended in a 50% glycerol, 0.01 M Tris buffered saline, pH 8.6, containing 0.7% formaldehyde (GTF) for examination under coverslips on glass slides.

Anti(Leu-5) binding to cells was demonstrated by an indirect fluorescence method in which 0.2 ml of cell suspension was pelleted by centrifugation. To this pellet was added 0.05 ml of PBS containing 5 μg of anti(Leu-5). The mixture was incubated 20 minutes at 4°, washed three times with PBS and again pelleted by centrifugation. To the pellet was added 0.05 ml of fluorescein labeled goat antimouse IgG (Cappel Laboratories, Cochranville, Pa.) diluted 1/10 in PBS. The mixture was incubated and washed with PBS as above and resuspended in GTF for examination.

To examine for surface Ig and anti(Leu-5) binding simultaneously, cells were first labeled with rhodamine conjugated goat antihuman IgG; washed twice and pelleted. The cell pellet was then incubated with anti(Leu-5) followed by fluorescein conjugated goat antimouse IgG as described above.

Labeled cells were examined on a Zeiss microscope fitted with an incident light source and interchangeable fluorescein, rhodamine excitation filters. Total cell counts of specimens were performed using transmitted light for illumination. A grid was placed in one ocular lens to facilitate counting.

Esterase staining of cells was as described by Yam et al., (1971) Am. J. Clin. Path. 55:2823. E-RFC were enumerated using the method of Bentwich et al., (1973) J. Exp. Med. 137:1532.

The anti(Leu-5) antibodies are potent inhibitors of human thymocyte rosette formation. These antibodies are 30 times less effective as inhibitors of rhesus thymocyte E-rosette formation as they are of human thymocytes. Anti(Leu-5) is able to mediate lysis of human thymocytes in the presence of rabbit complement, however, only at high concentrations. (Terasaki and McClelland (1964) Nature 204:998).

The AKR/j:NS 1 clone (anti(Leu-5) #3.2) grew exceptionally well when injected i.p. into AKR/j/Balb/c $F_1$ mice. After 14–20 days of growth as much as 10 ml of ascitic fluid could be collected from these mice. The average protein content of these fluids was 35 mg/ml of which 2 mg/ml was $IgG_3$.

A summary of anti(Leu-5) binding to various human and rhesus cell populations is given in Table 2.

TABLE 2

Anti(Leu-5) 3 Binding to Human Thymocytes, Monocytes, and PBL Subpopulations and to Rhesus Thymocytes and PBL

| Cell Population | % Neutrophils | % Ig+ | % Esterase+ | % E-RFC | % Null[1] | % Anti(Leu-5)[2] 3.1 | 3.2 |
|---|---|---|---|---|---|---|---|
| Human | | | | | | | |
| Thymocytes | 0 | 1 | 0 | 98 | 1 | 99 | 98 |
| Monocytes | — | 0 | 92 | — | — | 0 | 0 |
| PBL[3] | | | | | | | |
| Unseparated | 6 | 12 | 7 | 63 | 12 | 78 | 73 |
|  | 3 | 11 | 14 | 68 | 4 | 72 | 69 |
| E-RFC Enriched | 1 | 4 | 3 | 94 | 0 | 96 | 94 |
|  | 1 | 1 | 1 | 87 | 10 | 94 | 91 |
| E-RFC Depleted | 7 | 61 | 23 | 2 | 12 | 12 | 12 |
|  | 1 | 54 | 19 | 7 | 20 | 19 | 24 |
| Rhesus | | | | | | | |
| Thymocytes | 0 | 0 | — | 97 | 3 | — | 100 |
| PBL | 4 | 32 | — | 40 | — | — | 68 |

[1]Null cells calculated as 100 minus the sum of E-RFC, Esterase+, Ig+, and neutrophil percentages.
[2]% of cells which react with either anti(Leu-5) as determined by indirect immunofluorescence studies.
[3]Values given for each of two individuals studied.

Anti(Leu-5) 3.1 and 3.2 bound to thymocytes and PBL subpopulations in a similar fashion. Both antibodies bound to greater than 98% of human thymocytes and 75% of PBL. Ninety-eight and 65% respectively of these latter populations were capable of forming E-rosettes. Nearly all (95%) of E-RFC enriched PBL subpopulations were capable of binding anti(Leu-5). In contrast, only 20% of E-RFC depleted populations would bind anti(Leu-5). A substantially higher number of lymphocytes in the E-RFC depleted population bound anti(Leu-5) (12–24%) than formed E-rosettes (2–7%). However, the percentage of cells binding anti(Leu-5) in this latter subpopulation corresponded closely to the sum of the percent of cells forming E-rosettes and the null cell population (14-27%).

No binding of anti(Leu-5) antibodies to esterase positive, glass adherent human PBL (monocytes) could be detected, nor could anti(Leu-5) binding to human or rhesus erythrocytes or platelets be detected. No simultaneous staining of Ig+ or anti(Leu-5)+ cells was noted in unseparated PBL stained sequentially for Ig and anti(Leu-5).

A distinct pattern of staining was apparent on lymphocytes capable of binding anti(Leu-5). The antigen was evenly distributed over the cell surface in a speckled pattern with the specks varying in size from barely visible to almost plaque like.

A 0.05 mg sample of anti(Leu-5) 3.2 purified from ascitic fluid by binding and elution from protein A beads was labeled with $^{125}I$ (New England Nuclear, Boston, Mass.) according to the method of McConahey and Dixon, (1966) Int. Arch. Allergy Appl. Immunol. 29:185 to a specific activity of 0.003 mC/ng (3000 CPM/0.5 ng anti(Leu-5). $^{125}I$ anti(Leu-5) 3.2 was 94% TCA precipitable. The labeled antibody was used for binding studies to membranes prepared from human thymocytes, heart and erhthrocytes. Various concentrations of membrane protein in 0.5 ml of 0.1 M Tris buffered saline pH 8.6 were incubated one hour at room temperature with 4 ng (24,000 CPM) of $^{125}I$ anti(Leu-5) 3.2. Following incubation, the membranes were pelleted by centrifugation at 27,000×g for 15 minutes and a 0.1 ml aliquot of the supernatant counted in a gamma scintillation counter (Beckman Inst., Palo Alto, Calif.). Membrane bound label was calculated by subtraction of supernatant CPM from total CPM.

Thymocyte membranes were prepared by submitting thymocyte suspensions to negative pressure in a Stansted Cell Disruptor (Energy Service Co., Washington, D.C.) as described by Snary et al. (1974) Nature 247:457. Nuclei and debris were removed by centrifugation of disrupted cells at 500×g and membranes collected by further centrifugation of the supernatant at 27,000×g for one hour. Red blood cell ghosts were prepared by the method of Dodge et al. (1963) Arch. Biochem. Biophys. 100:119. Heart membranes were prepared from fresh recipient heart taken from cardiac recipients at time of transplant, tissue was minced into small pieces and homogenized in cold PBS using 10 second bursts of a Polytron Homogenizer (Brinkman Instruments, Westbury, N.Y.) at power setting 7. The heart membrane preparation was recovered by differential centrifugation as described above. All operations were quickly performed at 4° C. in PBS containing 4 $\mu$m phenylmethyl sulfonylfluoride to inhibit proteolysis. Membrane protein was measured by the method of Lowry et al. (1951) J. Biol. Chem. 193:265, using bovine albumin as a standard.

Fifty-six percent of $^{125}I$ anti(Leu-5) 3.2 bound to thymocyte membranes in contrast with less than 8% of the label separated or bound with equal proportions of membrane derived from heart or erythrocytes. Maximum absorption of 4 ng of labeled anti(Leu-5) 3.2 was achieved during a one hour incubation with 35 $\mu$g of thymocyte membrane protein. Further incubation of the absorbed supernatant with a fresh aliquot of thymocyte membrane resulted in no further absorption of label relative to background.

Administration of a single i.v. dose of either anti(Leu-5) 3.1 or 3.2 resulted in a pronounced lymphopenia in monkeys within one hour of treatment. In monkey 1003, who was given 1.5 mg/kg of anti(Leu-5) 3.1, lymphocyte levels fell from 2400 cells/mm$^3$ initially to a nadir of 325 cells/mm$^3$ at 4 hours. Total lymphocyte count in this animal returned to pretreatment levels by 24 hours. E-RFC fell from 1900 cells/mm$^3$ initially to non-detectable levels within 30 minutes but returned to approximately 50% of pretreatment level by 24 hours. Ig+ and PBL were not determined in animal 1003 therefore the nature of the nonrosetting lymphocytes could not be determined.

Lymphopenia in monkey 1009, who was given 1 mg/kg of anti(Leu-5) 3.2, was similar to that seen in 1003. The initial lymphocyte count of 4200 cells/mm$^3$ fell to a nadir of 1000 cells/mm$^3$ one hour following i.v. administration at anti(Leu-5) 3.2. E-RFC fell from an initial 1800 cells/mm$^3$ to undetectable levels within 30 minutes of dose administration and remained undetectable for the ensuring 4 days. Ig+ cells remained at fairly constant levels during the entire period of study and ranged from 700 to 1500 cells/mm$^3$. The null cell population rose from 800 cells/mm$^3$ initially to 1200 cells/mm$^3$ at 30 minutes to 0 at 1,2 and 4 hours. By 24 hours null cells had returned to approximately pretreatment levels and remained fairly constant thereafter.

In both animals there was an abrupt neutrophil leukocytosis which reached a zenith of about 11000 cells/mm$^3$ two to four hours following anti(Leu-5) administration. In both instances the neutrophil level returned to pretreatment levels within 24 hours. No other cellular abnormality was noted. In particular there was no change in the platelet count (3.1-4.8×10$^5$/mm$^3$). In both animals a slight hemo-concentrating effect was noted as evidenced by a rise in the blood hematocrit from 44 to 52%. Serum creatinine and BUN at no time rose significantly above pretreatment levels.

The Leu-5 antigen is believed to be a protein having a relative molecular weight of about 45,000 to 50,000. The anti(Leu-5) the antibodies of the subject invention appears to be specific for this antigen, which antigen appears to be involved in erythrocyte rosette formation.

The anti(Leu-5) mammalian monoclonal antibodies alone provide for analysis of blood cell population, but preferably in combination with other monoclonal antibodies, such as the antibodies binding to Leu-1 to Leu-4 as well as antibodies binding to other T cell antigens T-1 and T-3-3-10 as described by Reinherz and Schlossman, supra, a more intensive analysis can be made. Thus, blood cell populations can be characterized as to the nature, number, and maturity of lymphocytes present in the blood. Furthermore, the subject mammalian monoclonal antibodies can be used as immunosuppressants for allograft recipients, either of the same or different species from the mammalian lymphocytes used to prepare the hybridomas.

Although the foregoing invention has been described in some detail by way of illustration and example for purposes of clarity of understanding, it will be obvious that certain changes and modifications may be practiced within the scope of the appended claims.

What is claimed is:

1. Mammalian monoclonal antibodies specific for the lymphocyte antigen Leu-5, specifically binding to thymocytes and E-rosette forming peripheral blood lymphocytes and inhibiting human thymocyte rosette formation.

2. Antibodies according to claim 1, wherein said mammal is a mouse.

3. Mammalian monoclonal antibodies specific for the lymphocyte surface antigen Leu-5 having a label providing a detectible signal, specifically binding to human thymocytes and human peripheral blood lymphocytes which form E-rosettes and inhibiting E-rosette formation of human thymocytes.

4. Mammalian monoclonal antibodies according to claim 3, wherein said label is a member of the group consisting of a radioactive isotope, enzyme, fluorescent compound, chemiluminescent compound, ferromagnetic atom, or particle.

5. The mammalian monoclonal antibody according to claim 4, wherein said label is a radioactive isotope.

6. A mammalian monoclonal antibody according to claim 4, wherein said label is a fluorescent molecule.

7. A method for determining the presence of a cell suspected of containing a Leu-5 surface antigen, said method comprises combining a sample suspected of containing said cell having said Leu-5 surface antigen with mammalian monoclonal antibody according to claim 3; and detecting the presence of said Leu-5 by means of said signal provided by said label.

8. A method according to claim 7, wherein said label is a radioactive isotope.

9. A method for supressing the immunological response by a mammalian host to an immunogen which comprises introducing into said host a sufficient amount of mammalian monoclonal antibody according to claim 1 to suppress said immunological response.

* * * * *